United States Patent
Weiss et al.

(10) Patent No.: US 6,469,203 B1
(45) Date of Patent: Oct. 22, 2002

(54) METHOD FOR DEPOLYMERIZING POLYMETHYLMETHACRYLATE

(75) Inventors: Hans-Jürgen Weiss, Oberursel (DE); Jörg Schmalfeld, Bad Homburg (DE); Udo Zentner, Griesheim (DE); Tobias Groschang, Hanau (DE); Udo Gropp, Weinheim (DE); Werner Fuss, Karlstein (DE); Ralf Goedecke, Rodenbach (DE); Egbert Schöla, Müllendorf (AT)

(73) Assignees: Metallgesellschaft Aktiengesellschaft, Frankfurt/Main (DE); Rohm GmbH Chemische Fabrik, Darmstadt (DE)

( * ) Notice: Subject to any disclaimer, the term of this patent is extended or adjusted under 35 U.S.C. 154(b) by 0 days.

(21) Appl. No.: 09/787,088
(22) PCT Filed: Sep. 16, 1999
(86) PCT No.: PCT/EP99/06852
§ 371 (c)(1), (2), (4) Date: Jun. 21, 2001
(87) PCT Pub. No.: WO00/17149
PCT Pub. Date: Mar. 30, 2000

(30) Foreign Application Priority Data

Sep. 21, 1998 (DE) .......................................... 198 43 112

(51) Int. Cl.[7] .............................................. C07C 67/00
(52) U.S. Cl. ...................................... 560/216; 560/216
(58) Field of Search ......................................... 560/216

(56) References Cited

U.S. PATENT DOCUMENTS 3,959,357 A * 5/1976 Tokushige et al.
5,663,420 A * 9/1997 Vaughan et al.

* cited by examiner

*Primary Examiner*—Sreeni Padmanabhan
*Assistant Examiner*—Farhad Forohar
(74) *Attorney, Agent, or Firm*—Herbert Dubno; Jonathan Myers

(57) ABSTRACT

The present invention relates to a process of recovering monomeric esters of substituted or unsubstituted acrylic acid from polymer material having corresponding structural units by depolymerization by means of a fine-grained heat-transfer medium which is maintained above the depolymerization temperature of the polymer material. In a reactor, the polymer material is brought in contact with hot, mechanically fluidized heat-transfer medium. The resulting vapors are withdrawn and condensed, where the hot heat-transfer medium is continuously supplied at one end of the reactor, and cooled heat-transfer medium is discharged at the other end.

10 Claims, 1 Drawing Sheet

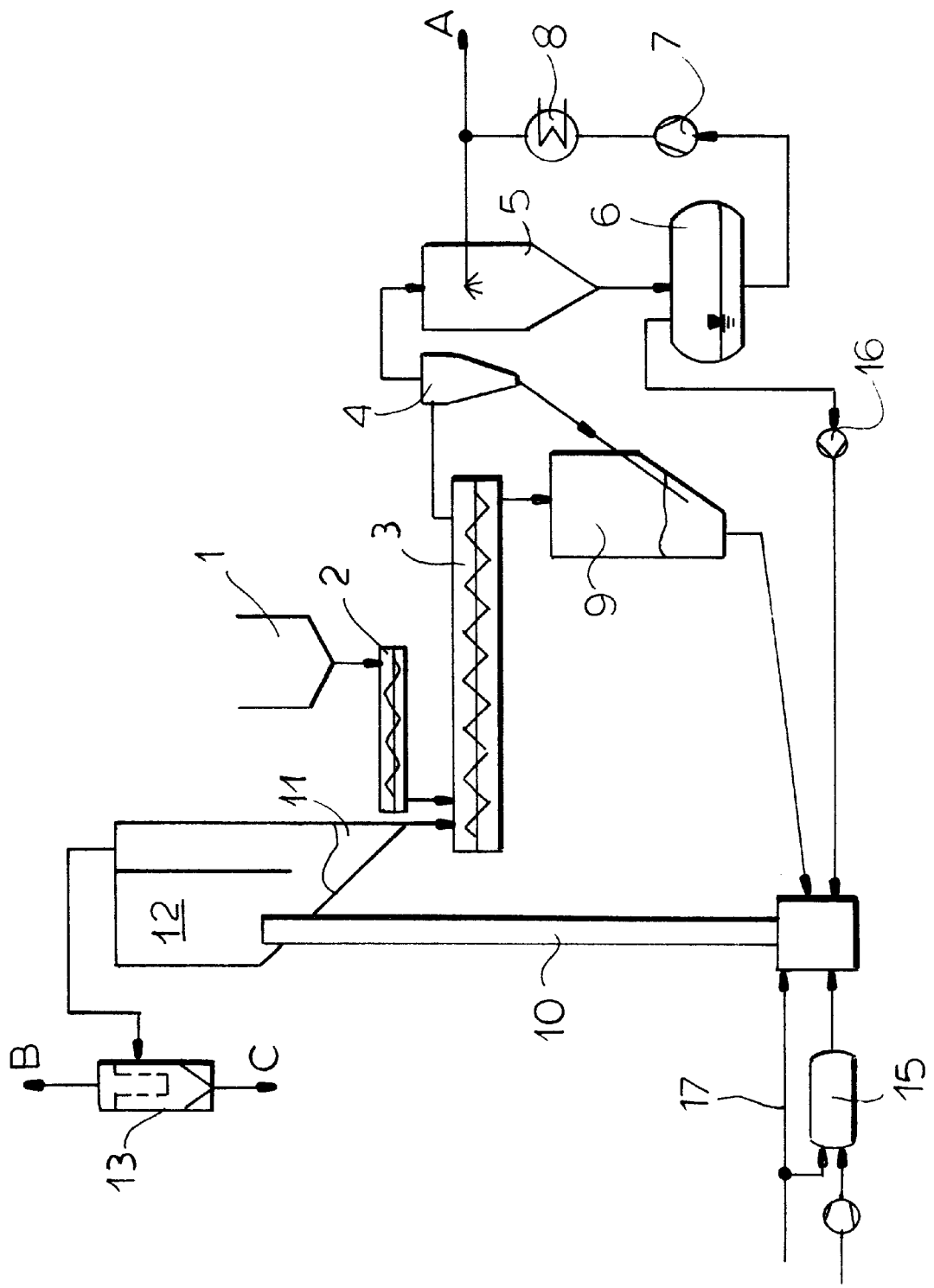

METHOD FOR DEPOLYMERIZING POLYMETHYLMETHACRYLATE

Process of Depolymerizing Polymethyl Methacrylate
This Application is a 371 of PCT/EP99/06852 filed on Sep. 16, 1999.

DESCRIPTION

The present invention relates to a process of recovering monomeric esters of substituted or unsubstituted acrylic acids from polymer material having corresponding structural units.

Acrylate polymers, which include acrylic glasses chiefly consisting of polymethyl methacrylate (PMMA), are used for instance for the production of long-lived consumer goods. For this purpose, there are frequently used molding processes in the course of which considerable amounts of waste polymer may be obtained. For expediently reprocessing these production wastes and for utilizing waste materials recirculated from the process of utilization quite a number of proposals have now been made.

It is a well-known fact that acrylate polymers, above all PMMA, belong to the few plastic materials which are excellently suited for direct chemical recycling. This means that at certain temperatures and pressures these polymers can completely be decomposed again into the corresponding monomer units (depolymerization) when heat is supplied in an appropriate way (Grassie, N., Melville, H. W., Bull. Soc. Chim. Belges 1948, p. 142).

In the reports on the "19. Kunststofftechnisches Kolloquium des Eurogress Aachen" (Mar. 11–13, 1998) there is described a continuously operating process of depolymerizing PMMA. The comminuted plastic material is charged into a hot extruder (ZSK 30), in which two tightly meshing screws are rotating with a self-cleaning effect. By means of these screws, nondepolymerized PMMA and other residues are discharged from the extruder. The PMMA will depolymerize in the extruder due to the thermal and the mechanical shearing effect. The resulting MMA is withdrawn as vapor phase through the degassing bell and is condensed. In this process, the MMA content of the condensate varies between 89% and 97%, the yield of MMA is about <97%. In the above-described process, heating the PMMA is effected in the extruder via the shell walls. The ratio of wall surface to reactor volume deteriorates, however, with increasing plant. For large plants on an industrial scale the available shell surface is so small that the extruder must either be made extremely hot, in order to sufficiently decompose the PMMA, or only very much worse yields of MMA are obtained. The necessary increased heating of the extruder shell, however, leads to a local overheating, which contributes to the formation of byproducts and impairs the monomer purity.

Furthermore, it is known to depolymerize PMMA by means of a fluidized-bed pyrolysis. As fluidized material there is used quartz sand having a grain size of 0.3 to 0.7 mm. It is a disadvantage of this process that in the course of time the fluidized material is graphitized with soot. When the soot chips off the sand grain, it can be entrained with the gas stream. To obtain an appealingly clean monomer, this plant therefore requires the implementation of many special filter systems (cooler, cyclone, electrostatic precipitator). In this method, a nitrogen stream is used for fluidizing the sand. It is likewise disadvantageous that after the depolymerization the nitrogen and the MMA gas must again be separated by cooling. The nitrogen stream, which upon separation from the product gas is recirculated to the reactor, must therefore be cooled and heated in constant alternation, where the temperature difference is at least 400 K. For a large-scale process, this is disadvantageous from an economical and ecological point of view (J. Franck, thesis 1993, Hamburg University).

It is the object of the invention to provide a process of recovering monomeric esters of substituted or unsubstituted acrylic acids from polymer material having corresponding structural units, which allows a continuous depolymerization free from residues, and thus provides for the production of high-quality recycled monomeric esters in a high yield. In accordance with the invention, free from residues is understood to be a process which avoids the formation of deposits in the reactor space and thus makes it superfluous to shut down the plant for removing the deposits, so that a continuous operation is ensured.

Furthermore, it is the object of the invention to provide a process as mentioned above, which can be operated on an industrial scale and helps to eliminate the disadvantages such as a poor transfer of heat during the depolymerization, a high amount of apparatus required as well as energetically unfavorable process flows.

The subject-matter of the invention is a process of depolymerizing PMMA, which is characterized in that in a reactor the polymer material is brought in contact with a hot mechanically fluidized solid (heat-transfer medium), and the resulting vapors are withdrawn and condensed, where the hot heat-transfer medium is continuously supplied at one end of the reactor, and cooled heat-transfer medium is discharged at the other end.

By means of the inventive process the reactor volume can be kept small as a result of the very good heat transfer of the fine-grained solid and the related relatively short dwell time of the polymer material. Hence, the dwell time of the resulting monomer vapors in the reactor is less than 6 seconds. The desired esters of the acrylic acids are obtained in very good yields and with a high purity. Thus, the hot, fine-grained heat-transfer medium also ensures that in large-scale plants a sufficient transfer of heat is ensured during the depolymerization.

In accordance with the invention, the mechanically fluidized fine-grained heat-transfer medium produces a rubbing effect in the reactor, which helps to completely prevent an accretion of byproducts resulting from the depolymerization at the inner walls and installations of the reactor. These depolymerization byproducts are continuously discharged from the reactor together with the fine-grained heat-transfer medium, so that an agglomeration of the byproducts in the reactor is prevented. Thus, it is possible to continuously perform the advantageous process, as no depolymerization residues, which otherwise must be removed from time to time from corresponding plants of the prior art, are left in the reactor. The monomer gas stream, which leaves the reactor, has a sufficient purity and need only be liberated from entrained dust particles by means of a cyclone. A separation from a carrier gas stream, which would even entrain more dust particles, is by no means necessary.

The mechanical fluidization and the transport of the fine-grained heat-transfer medium can be achieved by all possibilities well-known to the man skilled in the art, such as by moving or rotating walls, possibly under the influence of gravitation. There is preferred the embodiment where the substances supplied to the reactor are mechanically fluidized, mixed with each other and conveyed in a mixer by means of one or more intermeshing shafts rotating in the same direction, which are provided with coils or other mixing tools. Approximately the same dwell time of all solid particles (plug flow) in the range from 5 to 60 seconds can be adjusted by changing the rotational speed of the screws.

The polymer material is heated within a short period and depolymerized by means of the hot heat-transfer medium fluidized by the coils or mixing tools. The volatile components are discharged, whereas the solid byproducts remaining after the depolymerization are discharged from the reactor together with the heat-transfer medium, so that a contamination of the withdrawn monomer vapors with components originating from the solid byproducts is likewise very advantageously prevented. The mass balance of the heat-transfer medium in the reactor is preferably maintained by supplementing at the top end from a heated receiver.

As indicated above, the transport of the heat-transfer medium in the reactor can preferably be effected by one or more rotating shafts, which are equipped with coils or other mixing tools, from the inlet opening to the outlet opening.

Having been discharged from the reactor, the heat-transfer medium can be supplied to the bottom end of a pneumatic conveying line via a secondary degassing tank. The subsequent heating of the heat-transfer medium can basically be effected with all methods known to the man skilled in the art. Preferably, a hot, possibly oxygenous gas stream and/or possibly additional fuels are supplied to the bottom end of the pneumatic conveying line via the combustion chamber. The resulting gas stream supplies the heat-transfer medium to the top, where at the same time combustible residues from the depolymerization and additional fuels are burnt. Accordingly, this leads to the reheating of the fine-grained heat-transfer medium. The mixture of heat-transfer medium and gases reaches a heat transfer separator, from which gases and fine dust particles (e.g. color pigments contained in the PMMA) are withdrawn via a dust separator (cyclone, exhaust gas filter). The heat-transfer medium separated in the heat transfer separator trickles downwards and reaches a collecting tank which serves as hot heat transfer receiver for the reactor.

The temperature of the heat transfer solid at the reactor inlet depends on the ratio of the mass flows heat-transfer medium/polymer material. With a ratio of 10:1 a superheating of the heat-transfer medium of 150° C. is obtained, with a ratio of 5:1 a superheating of 300° C. During the depolymerization, the reaction mixing temperature of the heat-transfer medium can lie in the range between 300° C. and 650° C., preferably between 350° C. and 450° C. However, the heat-transfer medium heated by the hot gas stream has a temperature of 400° C. to 900° C., preferably 500° C. to 750° C.

As heat-transfer medium, every inorganic fine-grained solid (grain size between 0.1 and 5 mm, preferably 0.3 and 2.0 mm) can be used, which has the required strength and a sufficient stability with respect to temperature changes and oxygen. In many cases, screened sand was useful, which according to DIN 4222 is called coarse sand. However, there may also be used other naturally occurring or synthesized oxides on the basis of silicon, aluminium, magnesium, zirconium or also mixtures of these elements.

With the process in accordance with the invention, the dwell time of the vapors and gases formed in the reactor before the condenser can be less than 6 seconds, preferably less than 2 seconds. The dwell time of the fine-grained heat-transfer medium in the reactor is freely selectable. It is preferably in the range from 5 to 60 seconds.

The ratio of hot heat-transfer medium to PMMA in the reactor is likewise freely selectable in wide ranges. What seems to be expedient and preferred is a ratio between 3:1 and 30:1.

In accordance with a further aspect, the inventive process can improve the economy of the recovery as well as the quality of the product obtained in that the vapors withdrawn are treated with condensate, which was cooled in a monomer circulating cooler, and in that the condensate resulting from the treatment is recirculated to the cooler, where it is cooled and partly recirculated for treating the vapors withdrawn, and the remaining part of the condensate is discharged for further processing and product recovery.

The crude vaporous depolymerizate, i.e. the depolymerization gases, is first of all sprayed by means of a nozzle as in a shower with a part of the condensate previously cooled in the monomer circulating cooler and recirculated. Due to the direct contact of the depolymerization gases with the atomized crude condensate liquid a fast intensive cooling and a very short dwell time of the vaporous depolymerizate at the depolymerization temperature is achieved, which leads to a distinct improvement of the monomer yield and quality. The vapors withdrawn are quenched with condensate in a concurrent process. Solid deposits, which are produced on the otherwise usual coolers, can thereby be reduced considerably. Since the actual coolers only get in contact with a distinctly cooler, already condensed crude product, the risk of accretion or deposits is reduced. A reduction of the coating thickness on coolers can, however, additionally contribute to an improved quality of the crude condensate, in particular to an increased monomer content.

The condensate used for treating the monomer gases can be cooled in the monomer circulating cooler to a temperature between about 5 and 40° C., preferably 20 and 30° C. With parts of this cooled condensate, the vapors withdrawn from the reactor are then expediently cooled during quenching to a condensate temperature between 20 and 50° C., preferably 35 and 50° C.

The non-condensable vapors and gases of the condensate are expediently introduced into the riser, in which the fine-grained heat-transfer medium is heated, and also burnt.

In principle, the polymer material can be supplied to the reactor in every conceivable form. The commonly used introduction devices were successfully used in conjunction with conveyor belts, screws or the like. Larger pieces such as plates or molded articles can easily be comminuted to the size required or desired for the reactor, for instance by preceding shredders or mills. In the final analysis, the size of the processable polymer material pieces also depends on the properties of the polymerizates and the capacity of the reactor.

In general, the polymer material to be fed into the reactor and to be depolymerized there may be present in any conveniently processable form, for instance as chips, as granules, as fine powder, as shavings or as coarsely shredded material. These forms of addition may be introduced alone or in combination. Moreover, the more or less solid forms of addition can also be introduced together with liquid monomer in a more or less pure or contaminated form. When performing the invention, granules with a preferred grain size of about 1 to 10 mm were particularly useful.

The polymers to be fed into the reactor in the process in accordance with the invention chiefly contain structural units which in terms of their chemical structure satisfy the following formula I:

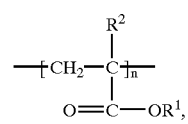

wherein
R$^1$ is C$_{1-6}$alkyl, preferably C$_{1-4}$alkyl,
R$^2$ is H, C$_{1-6}$alkyl, preferably H or C$_{1-4}$alkyl, with H or CH$_3$ being particularly preferred, and
n is a positive integer larger than 1.

Exemplary compounds include polymethyl acrylate, polyethyl acrylate, polymethyl methacrylate, polypropyl acrylate, polybutyl acrylate, polypropyl methacrylate, polybutyl methacrylate and copolymers which have two or more of these types of polymer. The first four compounds are preferred within the scope of the invention. Particularly preferred is polymethyl methacrylate (PMMA).

In addition to the chemical mixtures (random copolymers or also block copolymers), which were obtained by copolymerizing at least two substituted or unsubstituted acrylic-acid ester monomers (e.g. methylmethacrylate-n-butylmethacrylate copolymers), copolymers can be processed with the inventive process which have up to 50 wt-% of at least one further vinylically unsaturated monomer which can be copolymerized with at least one substituted or unsubstituted acrylic-acid ester monomer.

Typical examples include for instance methylmethacrylate-styrene copolymers or methylmethacrylate-butylacrylate-styrene terpolymers.

Physical mixtures, so-called blends, can also be reprocessed in accordance with the invention. As regards the reprocessing of polymer material in accordance with the inventive process, merely the fundamental possibility of the nondestructive depolymerization (with respect to the monomers) as well as the possibility of separating the resulting vapor mixture in a fractionated distillation or with other commonly used methods of separation must be seen as limiting factors. When depolymerization and separation are possible in principle, there is no fundamental obstacle to using the process in accordance with the invention.

BRIEF DESCRIPTION OF THE DRAWING

The invention will subsequently be explained in detail with reference to FIG. 1 of the drawing.

FIG. 1 shows a recipient vessel 1 for the polymer material, which at the top end is charged into a metering screw 2. With its end, the metering screw 2 opens into the top end of the reactor 3, which at this end also has a means for supplying hot heat-transfer medium from the receiver 11. At its end, the reactor 3 is on the one hand connected with a recipient vessel 9 (gas generator) for the discharged heat-transfer medium and on the other hand with a cyclone 4. From the cyclone 4, a further supply line opens into the condenser 5 which is connected with a monomer tank 6. Subsequent to the monomer tank 6 a monomer pump 7 is provided, which on the one hand supplies the condenser 5 via a monomer circulating cooler 8 and on the other hand provides product A to be discharged.

The dust separated in the cyclone 4 is recirculated to the gas generator 9, which in turn has a supply line to the riser 10. From the monomer tank 6, non-condensable gases are likewise supplied to the riser 10 via a blower 16, in which riser they are thermally disposed of (burnt).

Hot, oxygenous flue gas from the combustion chamber 15 and fuel from line 17 are still charged into the riser 10. The combustion chamber 15 is likewise supplied with fuel from line 17 and air from the blower 14. At the top, the riser 10 opens into the heat transfer separator 12, which has an outlet to a dust separator 13 (exhaust gas filter or cyclone) in which exhaust gas B and dust C are separated.

How the apparatus shown in FIG. 1 is operated can be taken from the following Example.

EXAMPLE IN ACCORDANCE WITH THE INVENTION

Via the polymer recipient vessel 1 1000 kg/h PMMA waste granules are metered into the reactor 3 via the metering screw 2. At the same time, 10,000 kg/h sand heated to about 550° C. are metered from the recipient vessel 11 into the reactor 3, in which the mixing of the above flows results in a depolymerization temperature of 400° C.

In the depolymerization, 5 kg/h solid residues as well as 995 kg/h gases and vapors are obtained, which are introduced into the condenser 5 via a cyclone 4, largely liberated from dust. In said condenser, they are charged with condensate, which was cooled to 25° C. in the monomer circulating cooler 8, and condensed before the condensate flows into the monomer tank 6. Via a pump 7, the monomer stream is pumped through the circulating cooler 8 and in part reused for the condensation of monomer vapors as well as guided to the discharge A in an amount of 990 kg/h. The 5 kg/h non-condensable gases obtained in the depolymerization are sucked off via the blower 16 and supplied to the riser 10, where they are burnt.

The 10,000 kg/h sand from the gas generator 9 together with the 5 kg/h residues from the depolymerization flow into the riser 10 with a temperature of 400° C. and by the hot gas formed in the combustion chamber 15 are pneumatically delivered into the heat transfer separator 12 via the riser 10 and reheated to 550° C. At the bottom end of the riser 10 additional fuel, e.g. heating oil, is added via line 17. By means of the excess atmospheric oxygen from the combustion chamber 15, the additional fuel as well as the organic depolymerization residue are burnt or oxidized. In the recipient vessel 11, the inorganic pigments and the heat transfer dust are separated from the coarser-grained sand by screening. The same is obtained in the receiver 11, whereas the flue gas and the fine dust get into the dust separator 13, where gas B is separated from dust C. The amount of MMA recovered from the condensate A is 958 kg/h (95.8% yield).

List of Reference Numerals:

| No. | Designation |
| --- | --- |
| A | MMA product stream |
| B | exhaust gas |
| C | dust |
| 1 | PMMA recipient vessel |
| 2 | metering screw |
| 3 | LR mixer-reactor |
| 4 | cyclone |
| 5 | condenser |
| 6 | monomer tank |
| 7 | monomer circulating pump |
| 8 | monomer circulating cooler |
| 9 | gas producer |
| 10 | riser |
| 11 | heat transfer receiver |
| 12 | heat transfer separator |
| 13 | dust separator |
| 14 | burner air blower |
| 15 | combustion chamber |
| 16 | exhaust gas blower |
| 17 | fuel line |

The reactor 3 of the Example is a LR mixer-reactor which is known per se, e.g. from "Erdoel und Kohle-Erdgas-Petrochemie/Hydrocarbon Technology" No. 42 (1989), pages 235–237. The reactor employs intermeshing shafts rotating in the same direction.

What is claimed is:

1. A process for continuously recovering a monomeric ester of a substituted or unsubstituted acrylic acid free from a depolymerization residue from a polymer material having corresponding structural units, which comprises the steps of:

(a) continuously supplying a hot heat transfer medium heated to a temperature between 400 and 900° C. to an inlet of a fluidizing reactor containing an inner wall and intermeshing rotating shafts which are provided with mixing tools;

(b) adding the polymer material having corresponding structural units to an inlet in the fluidizing reactor;

(c) depolymerizing in the fluidizing reactor at a temperature of 300 to 650° C. the polymer material with the hot heat transfer medium where the polymer material and the hot heat transfer medium are mechanically fluidized by intermeshing rotating shafts which are provided with mixing tools for rubbing the polymer material to prevent an accretion of a residue on the inner wall of the reactor, said residue resulting from the depolymerization of the polymeric material thereby preventing an agglomeration of the depolymerization residue in the reactor to obtain vapors of the monomeric ester of a substituted or unsubstituted acrylic acid free from the depolymerization residue and cooled heat transfer medium containing the depolymerization residue wherein the vapors of the monomeric ester have a dwell time in the fluidizing reactor of less than 6 seconds;

(d) continuously separately discharging from outlets in the fluidizing reactor the vapors of the monomeric ester of a substituted or unsubstituted acrylic acid free from the depolymerization residue and the cooled heat transfer medium containing the depolymerization residue; and (e) condensing the vapors of the monomeric ester of a substituted or unsubstituted acrylic acid free from the depolymerization residue to obtain a condensate free from the depolymerization residue and a non-condensable gas.

2. The process defined in claim 1 wherein according to step (a) the hot heat transfer medium has a grain size between 0.1 and 5 mm.

3. The process defined in claim 1 wherein according to step (a) the hot heat transfer medium is an oxide of silicon, aluminum, magnesium, zirconium, or mixtures thereof.

4. The process defined in claim 1 wherein according to step (c) the hot heat transfer medium in the fluidizing reactor has a dwell time that is freely selectable in the range of 5 to 60 seconds.

5. The process defined in claim 1 wherein according to step (c) the ratio of the hot heat transfer medium and the polymer material in the fluidizing reactor is freely selectable in the range of 3:1 to 30:1.

6. The process defined in claim 1 wherein according to step (e) the vapors of the monomeric ester of a substituted or unsubstituted acrylic acid free from the depolymerization residue are treated with condensate free from the depolymerization residue which was cooled in a monomer circulating cooler, and the condensate resulting from the condensation treatment is introduced into the monomer circulating cooler where the condensate is further cooled and in part recirculated for condensing additional quantities of the vapors of the monomeric ester of a substituted or unsubstituted acrylic acid free from the depolymerization residue, and the remaining part of the condensate is discharged for further processing and product recovery.

7. The process defined in claim 6 wherein the vapors are quenched with condensate in a concurrent process.

8. The process defined in claim 6 wherein the condensate used for treating the vapors of the monomeric ester is cooled in the monomer circulating cooler to a temperature between about 5° and 40° C.

9. The process defined in claim 1 wherein following step (e) the non-condensable gas is channeled to a riser leading to a heat transfer separator and the non-condensable gas is burnt in said riser to provide heat for heating additional hot heat transfer medium supplied during step (a).

10. A process for continuously recovering a monomeric ester of a substituted or unsubstituted acrylic acid free from a depolymerization residue from a polymer material having corresponding structural units, which comprises the steps of:

(a) continuously supplying a hot heat transfer medium heated to a temperature between 400 and 900° C. to an inlet of a fluidizing reactor containing an inner wall and intermeshing rotating shafts provided with mixing tools;

(b) adding the polymer material having corresponding structural units to an inlet in the fluidizing reactor;

(c) depolymerizing in the fluidizing reactor at a temperature of 300 to 650° C. the polymer material with the hot heat transfer medium where the polymer material and the hot heat transfer medium are mechanically fluidized by the intermeshing rotating shafts provided with mixing tools for rubbing the polymer material to prevent an accretion of a residue on the inner wall of the reactor, said residue resulting from the depolymerization of the polymeric material thereby preventing an agglomeration of the depolymerization residue in the reactor to obtain vapors of the monomeric ester of a substituted or unsubstituted acrylic acid free from the depolymerization residue and cooled heat transfer medium containing the depolymerization residue wherein the vapors of the monomeric ester have a dwell time in the fluidizing reactor of less than 6 seconds;

(d) continuously separately discharging from outlets in the fluidizing reactor the vapors of the monomeric ester of a substituted or unsubstituted acrylic acid free from the depolymerization residue and the cooled heat transfer medium containing the depolymerization residue;

(e) liberating the depolymerization residue from the cooled heat transfer medium by reheating the cooled heat transfer medium to a temperature between 400° C. and 900° C. by means of a hot gas stream, said hot gas stream moving the reheated heat transfer medium into a heat transfer receiver communicating with the fluidizing reactor;

(f) recycling the reheated heat transfer medium from the heat transfer receiver to the fluidizing reactor according to step (a); and (g) condensing the vapors of the monomeric ester of a substituted or unsubstituted acrylic acid free from the depolymerization residue to obtain a condensate free from depolymerization residue and a non-condensable gas.

* * * * *